United States Patent
Nefkens et al.

(12)

(10) Patent No.: US 6,194,400 B1
(45) Date of Patent: Feb. 27, 2001

(54) USE OF AMINO ACID PRECURSORS FOR THE TREATMENT OF ADDICTIONS

(76) Inventors: Gerard J. Nefkens; Helga Manuela Nefkens, both of GV Dormaalstraat 42, 3067 JH Rotterdam Holland (NL)

(*) Notice: Subject to any disclaimer, the term of this patent is extended or adjusted under 35 U.S.C. 154(b) by 0 days.

(21) Appl. No.: 09/283,228

(22) Filed: Apr. 1, 1999

(30) Foreign Application Priority Data

Apr. 10, 1996 (NL) ................................................ 1002833

(51) Int. Cl.$^7$ ............................................. A61K 31/5685
(52) U.S. Cl. ................................................... 514/178
(58) Field of Search .................................. 514/178

(56) References Cited

U.S. PATENT DOCUMENTS 4,518,595 * 5/1985 Coleman et al. ..................... 514/178

* cited by examiner

Primary Examiner—Phyllis G. Spivak
(74) Attorney, Agent, or Firm—Ronald P. Kananen; Rader, Fishamn & Grauer

(57) ABSTRACT

A method of treating addiction to a chemical, and products containing the chemical, is provided, which comprises administering to a human in need thereof, an effective amount of a pharmaceutical composition which comprises a sex steroid precursor. The chemical is one or more chemicals selected from the group consisting of nicotine, caffeine, alcohol, methadone, heroin, cocaine and subutex. The sex steroid precursor is selected from the group which comprises DHEA, DHEAS, analogues of DHEA, and analogues of DHEAS. A method of preparing a medicinally effective treatment for addiction to a chemical or to products containing the chemical is also disclosed, which includes synthetically producing or extracting a sex steroid precursor from a source where said sex steroid precursor was naturally produced in vivo, and combining an amount of the sex steroid precursor sufficient to effectively treat a human addiction to the chemical with a pharmaceutically acceptable carrier, excipient or agent.

19 Claims, No Drawings

USE OF AMINO ACID PRECURSORS FOR THE TREATMENT OF ADDICTIONS

FIELD OF THE INVENTION

The present invention is related to the treatment of human beings having various addictions, and the use of specific steroids for that purpose. Particularly, the present invention relates to treatment of nicotine-addicted people.

BACKGROUND OF THE INVENTION

Smoking tobacco has been proven in many case studies to cause cancer, and is linked with many other vascular diseases. Particularly, consumption of nicotine has been associated with arteriosclerosis, heart attacks, cerebral strokes, and various forms of cancer. While it is generally agreed that nicotine, when smoked or otherwise used for non-medicinal purposes, has extremely hazardous effects, the addictive nature of the drug causes many people to continue to use nicotine products to their detriment.

Various treatments have been developed that are designed to aid a person desiring to quit smoking. However, most of these treatments involve administering nicotine to individuals in a form other than a cigar or cigarette. while such a treatment may at times remove the craving for nicotine, these anti-smoking treatments are more harmful to those who continue to smoke during the treatment. Furthermore, the fact that nicotine is being replaced with nicotine provides at best the removal of a habit of lighting a cigar or cigarette and smoking it, but does not provide a relief from the cravings of nicotine. So far, no single effective method has been developed for the treatment of nicotine-addicted humans, and no effective pharmaceuticals have been disclosed.

Many publications are dedicated to the possible effects of the application to DHEA, DHEAS, and precursors of such. For simplicity, the term DHEA, unless otherwise noted, can be interpreted to include DHEAS and analogues and precursors of such as will be defined hereinafter. Some patent publications disclose various therapeutic effects of DHEA. European publication EP-0627921 teaches the use of DHEA as an anti-carcinogen. International publication WO-9416709 teaches the utility of DHEA for treatment of cancer of the uterus. WO-9408589 teaches treatment of lupus erythematosus using DHEA. WO-9494155 teaches the use of DHEA to treat eye diseases. Other scientific publications exist concerning the treatment of breast cancer, and obesity. An article in the Journal of Steroid Biochemistry and Molecular Biology concerned the blood concentrations of twenty different steroids in relation to the concentration of the interneural fluid low affinity interaction of steroids with neuronal membrane-bound receptors.

One study reported that low ESTRIOL and DHEAS levels were noticed in pregnant methadone addicted women (Eur. J. Obstet. Gynecol., vol. 23, p. 67 (1986)). It was concluded in the report that methadone (and probably heroin) use during pregnancy was accompanied by a reduction of circulating DHEAS levels. Although a link seems to exist between DHEA and methadone, there is no suggestion in the article or otherwise that administering DHEA might serve to cure methadone or heroin addiction, or any other addiction for that matter.

It is an object of the present invention to provide a medicinal treatment of addiction to smoking tobacco and any nicotine containing drug. It is a further object of the invention to provide a medicinal treatment of addiction to other substances where the addiction is related to consumption of material or foods that are not naturally part of the human body, such as coffee, tea, alcohol, and various other drugs. It is yet another object of the invention to provide such a treatment without including administration of the very substance to which the human is addicted.

SUMMARY OF THE INVENTION

The above objects and others are met by a method of treating addiction to chemicals and products containing addictive chemicals, which comprises administering to a human in need thereof an effective amount of a pharmaceutical composition which comprises a sex steroid precursor. Addictive chemicals that are applied against according to the present invention include nicotine, caffeine, alcohol, methadone, heroin, cocaine, and subutex. The sex steroid precursor can be any of DHEA, DHEAS, analogues of DHEA, and analogues of DHEAS, as well as compounds that serve as precursors to DHEA and DHEAS in vivo. Examples of analogues of DHEA and analogues of DHEAS comprise (n)-alphafluoroepiandrosterone, and bromoepiandrosterone.

Administering the treatment includes such methods as providing the sex steroid precursor sublingually, or otherwise causing the sex steroid precursor to enter into the bloodstream. The sex steroid precursor may be administered multiple times per day. In a preferred embodiment of the invention, the sex steroid precursor is administered at the times during the day when a person normally desires the addictive chemical.

The above described needs and others are also met by a method of preparing a medicinally effective treatment for addiction to a chemical and products containing the chemical, which includes the steps of extracting a sex steroid precursor from a source where the sex steroid precursor was naturally produced in vivo, and combining an amount of the sex steroid precursor sufficient to effectively treat a human addiction to a chemical and products containing such a chemical, with a pharmaceutically acceptable carrier, excipient, or agent. In the method, the step of combining the sex steroid precursors with a pharmaceutically acceptable agent may include fortifying foodstuff with the sex steroid precursors. The method may also include the step of mixing the sex steroid precursor with one of natrium hydroxybutyrate, and an amino acid containing compound selected from arginine, lysine, ornithine-HCL, and creatine. Other suitable amino acids may be suitable according to the needs of the patient.

As noted before, the addictive chemical includes one or more chemicals selected from the group which comprises nicotine, caffeine, alcohol, methadone, heroin, cocaine, and subutex. Also as noted before, the sex steroid precursor is selected from the group which includes DHEA, DHEAS, analogues of DHEA and DHEAS such as (n)-alphafluoroepiandrosterone, and bromoepiandrosterone.

Similarly, the above described needs and others are met by a method of preparing a medicinally effective treatment for addiction to a chemical and products containing said chemical, which includes the steps of providing at least one synthetically prepared sex steroid precursor, and combining an amount of the sex steroid precursor sufficient to effectively treat a human addiction to a chemical and products containing the chemical, with a pharmaceutically acceptable carrier, excipient, or agent. The step of combining the sex steroid precursors with a pharmaceutically acceptable agent may include fortifying foodstuff with the sex steroid precursors.

The method may further include the step of mixing the sex steroid precursor with at least one of vitamin E, vitamin C, and coenzyme units. Furthermore, the method may include the step of mixing the sex steroid precursor with one of natrium hydroxybutyrate, and an amino acid containing compound selected from arginine, lysine, ornithine-HCL, and creatine.

As in the prior methods, the addictive chemical is one or more chemicals selected from the group which comprises nicotine, caffeine, alcohol, methadone, heroin, cocaine, and subutex. Also, the sex steroid precursor is selected from the group which includes DHEA, DHEAS, and precursors of the compounds such as (n)-alphafluoroepiandrosterone, and bromoepiandrosterone.

DESCRIPTION OF THE PREFERRED EMBODIMENT

The following is a detailed description of the present invention, and how the present invention serves to accomplish the above objects and others. The present invention includes a method of treating addicted human beings and the use of specific steroids for that purpose. Particularly, the invention includes a method for treatment of nicotine-addicted people and the use of sex steroid precursors for that purpose. Accordingly, the present invention includes a method of preventing tobacco and nicotine related diseases such as cancer, vascular diseases and other related illnesses and diseases such as arteriosclerosis, heart attacks, cerebral strokes, etc.

The sex steroid precursors deyhdroepiandrosterone (DHEA) and dehydroepiandrosteronsulfate (DHEAS) are major natural adrenal secretory products in humans. The compounds are converted in vivo into active hormones such as testosterone and estrogen. These end products are essential for many critical functions such as regulating libido and metabolism, for example. Because the sex steroid precursors are converted in vivo into active hormones they are indicated in this specification as precursors. DHEA and DHEAS can be produced synthetically, as well as naturally, or, in vivo.

Analogues of the above mentioned sex steroid precursors are synthetically prepared molecules such as flouro- or bromo-epiandrosterone. Certain analogues can be converted in vivo into one of the above mentioned sex steroid precursors, their active components or hormones. As previously mentioned, for convenience in this specification, the term DHEA also refers to the above mentioned sex steroid precursors and analogues.

The plasma concentration of DHEAS which is the second abundant steroid in humans, undergoes the most marked age-related decline of any known steroid. In the body of a 25 year old human, DHEAS is abundantly present. Specifically, a 25 year old female has in her blood about 4.5 micrograms per milliliter, and a 25 year old man has in his blood about 7.9 micrograms per milliliter. After the mid twenties, the concentration of DHEAS in a person naturally lowers. For example, at the person's age of about 80, the concentration of DHEAS in the bloodstream is about 10% of its concentration when the person was the age of 25. The body uses these precursors to create sex hormones, but it is presumed that these precursors are also engaged in other metabolic activities.

Surprisingly, it has been observed by the inventor that addiction to nicotine or other addictive drugs can be cured by administering, or otherwise introducing an effective amount of DHEA into the bloodstream of a person. It has also been discovered that DHEA can be used for the preparation of a medicine, and therapeutically used for the detoxification of people from addicting substances, particularly nicotine.

It is pointed out that for each individual the proper level of DHEA for effective treatment of an addiction must be singly established. Most of the time, a sufficient treatment includes bringing the concentration of DHEA in the person's bloodstream to a level that is higher than the average concentration of DHEA in the bloodstream of people the age of the addicted person. While an "overdose" of the DHEA, relative to the average concentration of DHEA in people of the same age as the addicted person has been found to have a maximum effect, it is not necessarily true that the overdose should induce a concentration of DHEA in the person's bloodstream above that which is normally found in youths.

A principle advantage of the invention is the observation that when the effective dose of DHEA is used, the detoxification process is easy and painless for the person being administered the DHEA. Another advantage of the present invention is the observation of long standing effectiveness and the safety of the treatment. In treatments performed as tests by the inventor to randomly chosen individuals, following the successful treatment of the individuals there was little or no involuntary returning to the habit based on cravings of an addictive chemical. Furthermore, because of the high level of safety of the treatment, any recurrence of the habit can immediately be treated using the same treatment previously administered.

However, the recurrence of the habit is unlikely following treatment according to the present invention due to the fact that in the case of nicotine, for example, a person normally has an inherent disgust against smoking following the treatment. In the case of other addictive chemicals such as caffeine and alcohol, such feelings of disgust toward the chemical are present, although not as intensely, toward a level of indifference to the chemicals.

In a preferred embodiment of the invention, the treatment is administered by at least partially consuming the DHEA sublingually. The effective dosage typically ranges between 100 and 300 milligrams per day, and is divided into small doses taken many times per day. For example, a 30 milligram dose may be administered 10 times per day.

Regular medical control is recommended, including blood analysis, to ensure the absence of high levels of prostate specific antigen (PSA check). Furthermore, it is sometimes desirable to combine the treatment with antioxidants such as vitamin E, vitamin C, and coenzymes such as coenzyme Q10. The administration of coenzymes concurrent with DHEA may improve the liver flow during detoxification, especially among people who have already suffered liver problems.

Furthermore, people with smoking and other chemical dependencies have acquired heart diseases. Accordingly, the combination of the DHEA treatment with muscle enforcing products may serve to double the benefits of the treatment of the present invention. Such muscle enforcing products include natrium hydroxybutyrate (GHB) and amino acid supplements such as arginine, lysine, ornithine-HCl, creatine, etc.

Gradual reduction of the dosage over an appropriate amount of time will serve to counter any addiction to DHEA that may develop over prolonged treatment. It is to be understood, however, that addiction to DHEA and the other precursors and analogues described herein are very slight. Furthermore, sex steroid precursors are generally agreed, in scientific literature, to be harmless, especially to humans having acceptable PSA levels.

The positive effects of the treatment of the present invention could be diminished by parallel intake of hormones and possibly by the consumption of meat, because of a possible presence of non- or anti-coherent hormones. Accordingly, the administration of the treatment should necessarily be under medical control in order to ensure a safeguard in respect to the quality and origin of the precursors administered.

EXAMPLES

A male human being was administered a sublingual intake of 10 doses, 30 mg each dose, of DHEA daily. The sublingual intake was administered normally at times during the day when the person desired a cigarette. The person was 59 years old, 1.8 meters in height, and 84 kilograms in weight. Data showed that the person was generally healthy, and conducted a busy, hectic lifestyle. The person smoked tobacco to some degree for 40 years prior to the treatments, and for about twenty of the 40 years he smoked at least 70 cigarettes per day. In addition, the person consumed coffee at an average of about 1 liter per day. The person had, prior to the treatments, unsuccessfully attempted to quit both smoking tobacco and drinking coffee on numerous occasions.

Following the first day of treatment of the above doses of DHEA, a slight yet traceable indifference for cigarettes and consumption of coffee was observed. Attraction to other substances such as tea, chocolate, sugar and alcohol was also diminished over the weeks of treatment.

Following three weeks of treatment, the person had greatly reduced his cigarette use. The person positively indicated that the reduction in the amount of cigarettes smoked resulted without any effort on his part. After only eight weeks of the treatment, the person indicated a definite resentment of cigarettes or tobacco generally.

During the first year following beginning of administration of the above doses of DHEA, treatments were abruptly stopped on five different occasions as a test. Each time that treatment was stopped, the person would grieve for the above mentioned products, including tobacco, alcohol, coffee, tea, chocolate, and sugar generally. However, each time the treatment was abruptly stopped, the person's grieving for these substances became less intense.

Following 10 months of the above treatment, the intake of DHEA was reduced to 200 milligrams per day. After 15 months from the start of the treatment, the intake of DHEA was reduced to 100 milligrams per day, in about 6 or 7 sublingual pills of 15 milligrams DHEA each.

After nearly two years of treatment, the total amount of DHEA administered to the person per day was as little as 5 milligrams. The person reportedly had no desire to smoke, and considered cigarettes and the associated smell of cigarette smoke to have no inviting value. Furthermore, the person's intake of other drugs such as caffeine in the form of coffee was significantly reduced to about 2 cups per day.

Having described an embodiment of the invention, it is to be understood that the invention is not limited to any of the precise embodiments described herein. Various changes and modifications could be effected by one skilled in the art without departing from the spirit or scope of the invention as defined in the appended claims.

What is claimed is:

1. A method for treating addiction to a chemical and products containing said chemical, which comprises administering to a human in need thereof, an effective amount of a pharmaceutical composition which comprises a sex steroid precursor, wherein said chemical is one or more chemicals selected from the group consisting of nicotine, caffeine, alcohol, methadone, heroin, cocaine, and subutex.

2. A method as set forth in claim 1, wherein said chemical is nicotine.

3. A method as set forth in claim 1, wherein said sex steroid precursor is selected from the group which comprises DHEA, DHEAS, analogues of DHEA, and analogues of DHEAS.

4. A method as set forth in claim 3, wherein said analogues of DHEA and analogues of DHEAS comprise (n)-alphafluoroepiandrosterone and bromoepiandrosterone.

5. A method as set forth in claim 1, wherein said administering comprises providing said sex steroid precursor sublingually.

6. A method as set forth in claim 1, wherein said administering comprises providing said sex steroid precursor multiple times per day.

7. A method as set forth in claim 6, wherein said sex steroid precursor is administered at any time said human desires said chemical.

8. A method of preparing a medicinally effective treatment for addiction to a chemical and products containing said chemical, which comprises:

extracting a sex steroid precursor from a source wherein said sex steroid precursor was naturally produced in vivo; and combining an amount of said sex steroid precursor sufficient to effectively treat a human addiction to a chemical or to products containing said chemical, with a pharmaceutically acceptable carrier, excipient, or agent.

9. A method as set forth in claim 8, wherein said combining said sex steroid precursors with a pharmaceutically acceptable agent comprises fortifying foodstuff with said sex steroid precursors.

10. A method as set forth in claim 8, which further comprises mixing said sex steroid precursor with one of natrium hydroxybutyrate, and an amino acid containing compound selected from arginine, lysine, ornithine-HCl, and creatine.

11. A method as set forth in claim 8, wherein said chemical is one or more chemicals selected from the group consisting of nicotine, caffeine, alcohol, methadone, heroin, cocaine, and subutex.

12. A method as set forth in claim 8, wherein said sex steroid precursor is selected from the group which comprises DHEA, DHEAS, analogues of DHEA, and analogues of DHEAS.

13. A method as set forth in claim 12, wherein said analogues of DHEA and analogues of DHEAS comprise (n)-alphafluoroepiandrosterone, and bromoepiandrosterone.

14. A method of preparing a medicinally effective treatment for addiction to a chemical and products containing said chemical, which comprises:

providing at least one synthetically prepared sex steroid precursor; and combining an amount of said sex steroid precursor sufficient to effectively treat a human addiction to a chemical or to products containing said chemical, with a pharmaceutically acceptable carrier, excipient, or agent.

15. A method as set forth in claim 14, wherein said combining said sex steroid precursors with a pharmaceutically acceptable agent comprises fortifying foodstuff with said sex steroid precursors.

16. A method as set forth in claim 14, which further comprises mixing said sex steroid precursor with at least one of vitamin E, vitamin C, and coenzyme units.

17. A method as set forth in claim 14, which further comprises mixing said sex steroid precursor with one of natrium hydroxybutyrate, and an amino acid containing compound selected from arginine, lysine, ornithine-HCL, and creatine.

18. A method as set forth in claim 14, wherein said chemical is one or more chemicals selected from the group consisting of nicotine, caffeine, alcohol, methadone, heroin, cocaine, and subutex.

19. A method as set forth in claim 14, wherein said sex steroid precursor is selected from the group which comprises DHEA, DHEAS, (n)-alphafluoroepiandrosterone, and bromoepiandrosterone.

* * * * *